(12) United States Patent
Schilling et al.

(10) Patent No.: US 9,146,216 B2
(45) Date of Patent: Sep. 29, 2015

(54) DEVICE FOR SAMPLE PREPARATION

(75) Inventors: Beat Schilling, Zurich (CH); Bernhard Fischer, Anwil (CH); Georg Hottinger, Horgen (CH); Markus Meier, Wenslingen (CH)

(73) Assignee: BGB Analytik AG, Bockten BL (CH)

( * ) Notice: Subject to any disclaimer, the term of this patent is extended or adjusted under 35 U.S.C. 154(b) by 126 days.

(21) Appl. No.: 10/581,951

(22) PCT Filed: Dec. 15, 2004

(86) PCT No.: PCT/CH2004/000689
§ 371 (c)(1),
(2), (4) Date: Aug. 25, 2006

(87) PCT Pub. No.: WO2005/057206
PCT Pub. Date: Jun. 23, 2005

(65) Prior Publication Data
US 2007/0113616 A1   May 24, 2007

(30) Foreign Application Priority Data

Dec. 9, 2003  (CH) ..................................... 2095/03

(51) Int. Cl.
*G01N 30/18* (2006.01)
*G01N 1/40* (2006.01)
*G01N 30/06* (2006.01)
*G01N 30/12* (2006.01)

(52) U.S. Cl.
CPC .............. *G01N 30/18* (2013.01); *G01N 1/405* (2013.01); *G01N 2030/062* (2013.01); *G01N 2030/121* (2013.01)

(58) Field of Classification Search
CPC . G01N 1/405; G01N 30/18; G01N 2230/062; G01N 2030/121
USPC ................. 73/864.71, 864.74, 23.41, 863.21, 73/864.87
See application file for complete search history.

(56) References Cited

U.S. PATENT DOCUMENTS

| | | | | |
|---|---|---|---|---|
| 3,929,130 A | * | 12/1975 | Hargest | ........................... 604/28 |
| 4,563,893 A | * | 1/1986 | Tanyolac et al. | ............. 73/23.34 |
| 4,793,920 A | * | 12/1988 | Cortes et al. | ................ 210/198.2 |
| 4,849,179 A | * | 7/1989 | Reinhardt et al. | .............. 422/89 |
| 5,064,418 A | * | 11/1991 | Cronin | .......................... 604/190 |
| 5,123,276 A | | 6/1992 | Hartman et al. | |

(Continued)

FOREIGN PATENT DOCUMENTS

| | | |
|---|---|---|
| CH | 656 957 | 7/1986 |
| DE | 195 25 771 | 3/1996 |

(Continued)

OTHER PUBLICATIONS

Peters, T.L. (1997) A Syringe Mountable Micro Adsorbent Column for the Concentration of Organics. Research Disclosure, Kenneth Mason Publications. 399:453.

*Primary Examiner* — Daniel S Larkin

(57) ABSTRACT

The invention relates to a method, particularly suitable for the extraction and enrichment of a volatile component from a liquid, solid or gaseous sample for subsequent introduction into an analytical device, for example, a gas chromatograph. The sample is flushed through a packing of extraction material for extraction of the analytes of interest. A suitable device comprises a syringe with a hollow needle. A chamber is provided between the needle and syringe, in which the extraction material is arranged.

2 Claims, 5 Drawing Sheets

(56) References Cited

U.S. PATENT DOCUMENTS

Figure 1:
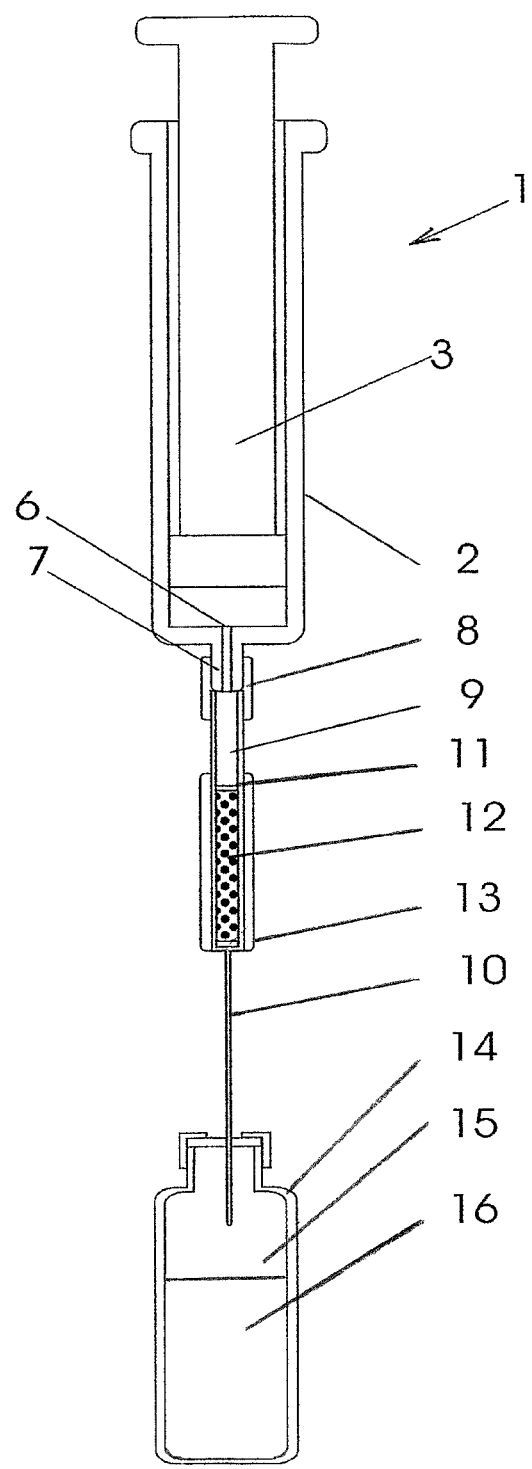

| | | | |
|---|---|---|---|
| 5,391,288 A * | 2/1995 | Collins et al. | 208/89 |
| 5,565,622 A | 10/1996 | Murphy | |
| 5,595,653 A * | 1/1997 | Good et al. | 210/289 |
| 5,620,603 A * | 4/1997 | Betz et al. | 210/635 |
| 5,693,228 A * | 12/1997 | Koehler et al. | 210/656 |
| 5,919,356 A * | 7/1999 | Hood | 210/85 |
| 5,965,803 A * | 10/1999 | Chinn et al. | 73/23.34 |
| RE36,811 E * | 8/2000 | Markell et al. | 210/638 |
| 6,397,658 B1 * | 6/2002 | Villettaz et al. | 73/19.12 |
| 6,566,145 B2 * | 5/2003 | Brewer | 436/178 |
| 6,825,046 B1 * | 11/2004 | Forsyth | 436/178 |
| 6,834,531 B2 * | 12/2004 | Rust | 73/23.41 |
| 2001/0032521 A1 | 10/2001 | Pawliszyn | |
| 2004/0091400 A1 * | 5/2004 | Wada et al. | 422/101 |
| 2005/0233085 A1 * | 10/2005 | Miller et al. | 427/372.2 |

FOREIGN PATENT DOCUMENTS

| | | | |
|---|---|---|---|
| DE | 100 24 443 | 11/2001 | |
| JP | 10-10104 A * | 1/1998 | |
| WO | WO 99/31480 | 6/1999 | |
| WO | WO 00/75623 A1 * | 12/2000 | |
| WO | WO 03/019149 A1 * | 3/2003 | 436/177 |

* cited by examiner

DEVICE FOR SAMPLE PREPARATION

The invention relates to a method for preparation of a sample, in particular for extraction and enrichment of a volatile component from a liquid, solid or gaseous sample for subsequent introduction into an analytical device, for example a gas chromatograph. A device for carrying out this method comprises a syringe, and a hollow needle connected to the syringe body.

To allow components of interest from a sample, for example volatile impurities from an environmental sample, to be analyzed in a gas chromatograph, the sample has to be prepared in such a way that the components of interest are extracted from the sample and enriched. DE 19525771 discloses a solid-phase extraction which uses a syringe to transfer the components of interest into a chromatograph, the needle of said syringe being provided with a coating of a stationary phase. By suctioning a sample into the needle, if appropriate several times, an extraction of components of interest takes place. The components detached by desorption from the stationary phase are then introduced into the injection inlet of a gas chromatograph. The syringe can be operated manually or automatically.

A similar device with a syringe whose needle is coated with a stationary phase is known from WO99/31480. In this device, a delivery system is additionally provided for a carrier gas which is inert in relation to the analyte and by means of which the components of interest are desorbed and delivered to a gas chromatograph. DE10024443 likewise describes a device with a syringe whose needle has a coating of a stationary phase on which the analyte of interest adsorbs and is then introduced by desorption into a gas chromatograph. For this purpose, the needle is flushed with a carrier fluid during the desorption phase.

These known systems have the disadvantage that, because of the limited surface (a few mm$^2$) of the extraction material, the extraction, i.e. the uptake of the components of interest, is slow and incomplete. For this reason, the efficiency of these known systems is not optimal. Therefore, the object of the invention is to remedy this disadvantage.

According to the invention, this is achieved by a method of the type mentioned at the outset, which is characterized in that the sample is flushed through an extraction material for extraction of the analytes of interest. A device for carrying out this method is characterized in that, between the needle and the syringe body, a chamber is provided which is wider than the cross section of the needle and in which an extraction material is located.

According to a preferred embodiment of the invention, the extraction material comprises particles or beads coated with stationary phase (e.g. CHROMOSORB® (chromatographic stationary support material made from mined diatomite) coated with CARBOWAX 20M® (additional polymers of ethylene oxide and water and their ethers)). According to another preferred embodiment, the extraction material comprises absorption materials such as are used in chromatography (e.g. CARBOSIEVE S3® (activated carbon), CARBOPACK® (porous graphitized carbon black), TENAX® (carbon fiber), activated charcoal, etc.).

Preferred illustrative embodiments of the invention are described below with reference to the attached drawings, in which:

FIG. 1 shows a cross section through an embodiment of the device according to the invention, and FIGS. 2-5 show schematic representations of different method sequences.

As is shown in FIG. 1, a gastight syringe 1 comprises a syringe body 2, and a plunger 3 which is axially movable in the latter. At its lower end, the syringe body has, as usual, an outlet opening 6 with a connector 7, which is configured as a Luer connector for example. An extraction tube 9 is connected to the connector 7 by means of an attachment piece 8. Arranged at the lower end of the extraction tube is the hollow needle 10 which, in standard syringes, would be fitted onto the Luer connector 7.

Alternatively, it is possible for the extraction tube and the hollow needle to be produced in one piece.

The extraction tube 9 has a diameter of between 0.5 and 4 mm and a length of 2 to 60 mm. In its interior, a packing 12 is located between two hoops 11. The hoops are made of sintered metal beads. Alternatively, other materials can also be used for the hoops, for example tufts of glass wool, metal screens, etc.

For the purpose of this description, the terms extraction material is to be understood as meaning that at least part of the interior of the extraction tube 9 between the hoops 11 is filled in the manner of a packing with the material. As extraction material, particles are used which are of the kind used as absorbents or as packing materials in gas chromatography, for example TENAX® (carbon fiber), CHROMOSORB® (chromatographic stationary support material made from mined diatomite), CARBOPACK® (porous graphitized carbon black), activated charcoal, etc. All the materials used, whether organic or inorganic, have the common property that molecules are adsorbed on their surface and are thus able to accumulate.

The extraction tube 9 is provided with a heating jacket 13. The heating permits thermal desorption. Instead of the heating jacket, radiant heating or direct heating of the tube with low voltage and relatively high current strength is possible.

The typical procedure with the device described here is as follows: The sample 16 to be analyzed is generally located in a gastight sample vial 14. Some of the gas located in the space 15 above the sample (the head space) is sucked through the extraction material with the aid of the syringe, whereby the molecules to be analyzed (analyte) are absorbed on the surface and accumulate there after a quantity of gas has been drawn in several times. In a further step, these molecules are fed to an analytical device (e.g. a gas chromatograph), either by the extraction tube being heated and having gas passed through it (thermal desorption), or the analyte being washed from the particles by a solvent and being delivered with the solvent to the analytical device (liquid desorption).

Figure 2:
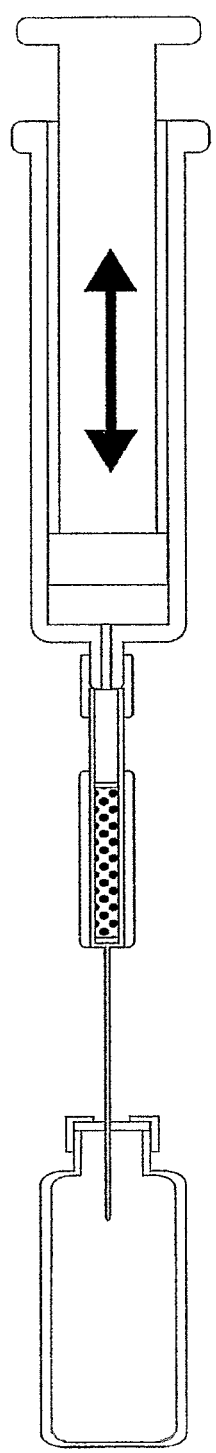

The method is carried out using a liquid sample, specifically in the manner shown in FIGS. 2 to 4, as follows:

First, the sample is prepared or worked up by means of the molecules to be analyzed, i.e. the analyte, being separated from the liquid. There are three preferred possible ways of doing this:

Either, as is shown in FIG. 2, the syringe needle is introduced into the gas space of the sample vial. By repeated intake and ejection of the gas with the syringe, the substances to be analyzed are transferred at least partially to the extraction material.

Figures 3A, 3B:
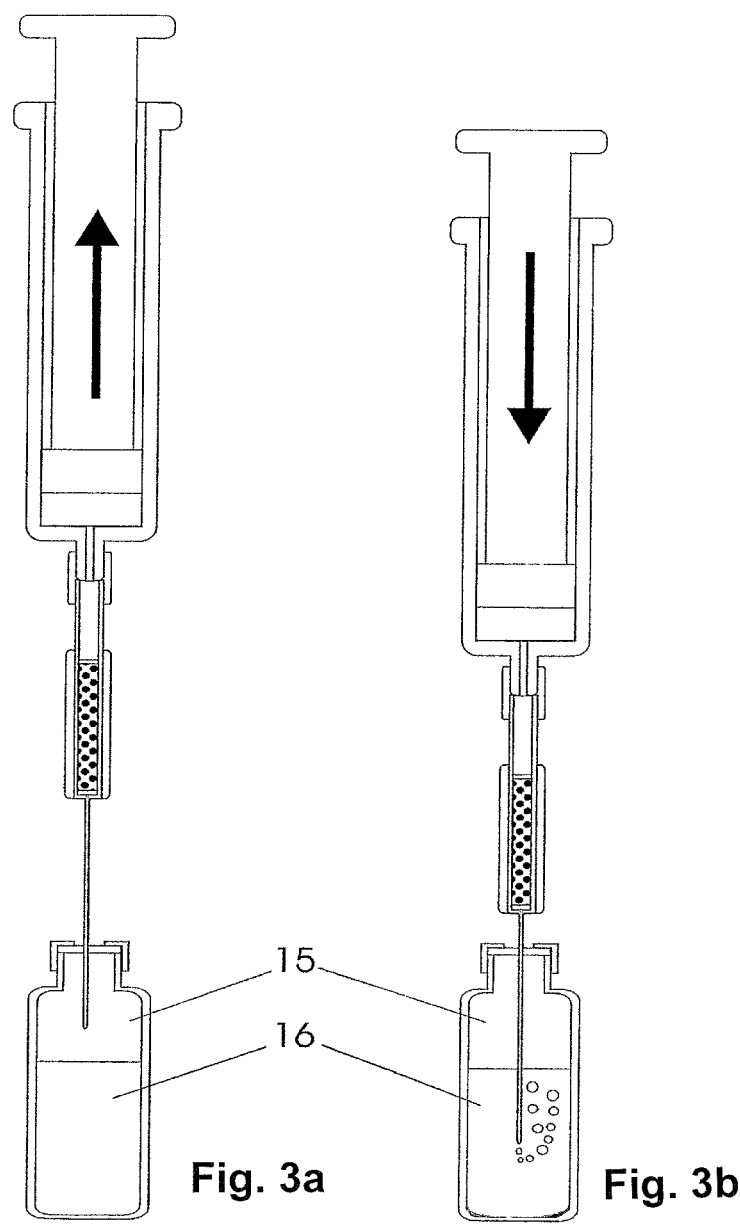
Figure 4:
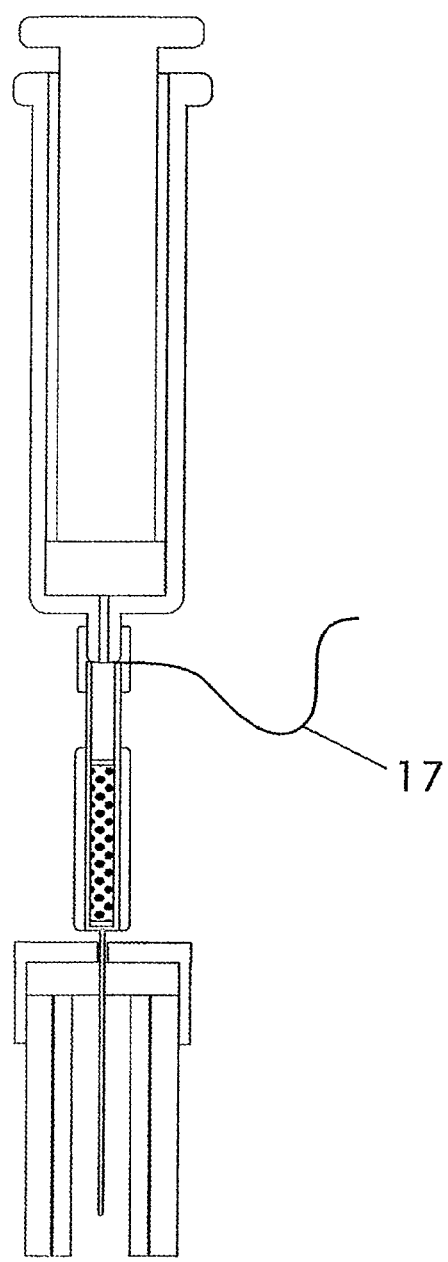

Or, as shown in FIGS. 3a and 3b, the tip of the syringe needle is first introduced into the gas space 15 of the sample vial 14 and some of the gas is drawn into the syringe using the syringe. The needle tip is then immersed in the liquid 16 and the gas expelled, whereupon volatile molecules are blown from the liquid into the gas space. Thereafter, the needle tip is then drawn back again into the gas space and some of the gas is drawn into the syringe through the extraction material. This procedure can be repeated in order to increase the efficiency of the extraction.

As a third alternative, the liquid can be drawn directly through the extraction material into the syringe. This procedure too can be repeated in order to heighten the efficiency.

The first of the three described procedures is used to work up a solid sample.

To avoid contamination of the system by ambient air, the syringe can be partly filled with clean gas before being introduced into the sample vial.

To transfer the substances into the analytical device, thermal desorption or liquid desorption is used. Thermal desorption is based on the fact that the substances deposited on the particles detach again from the particles at elevated temperatures and convert to the gaseous phase. If the extraction material is heated and gas is conveyed through it, the substances to be analyzed can be transferred in this gaseous stream into the analytical device. In liquid desorption, the substances are detached from the particles with a solvent and transferred to the analytical device.

For thermal desorption, there are once again several possibilities, in each case with simultaneous heating of the packing. It can either be carried out, as is shown in FIG. 4, by delivering a clean gas through a gas inlet 17 arranged between the syringe and the packing. This procedure is the most elegant, but also the most complicated way of bringing the substances from the filter into the gas chromatography. Since the syringe plunger is pressed fully down and the lateral gas admission line has only a very small volume during the injection, the danger of gas flowing in the wrong direction is negligible. The desportion gas pressure must be slightly higher than the gas pressure in the injector. In this procedure, the substances are moreover transferred gently into the analytical device, because only gas that is free of oxygen can be used. However, the procedure requires an additional valve and a pressure control means, i.e. a certain level of expenditure in terms of equipment.

Figure 5:
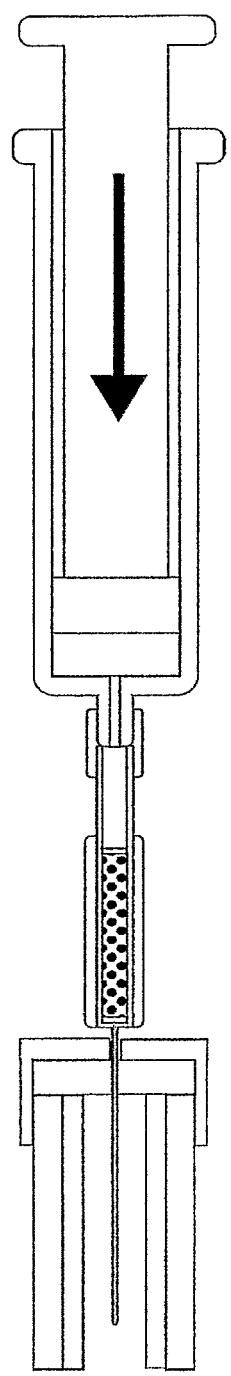

Alternatively, as is shown in FIG. 5, it can be carried out using gas from the sample vial. This procedure is technically the simplest, since no additional gas valves or appliances are required. However, it has the disadvantage that the substances to be analyzed are exposed to higher temperatures and oxygen during the desorption, which can lead to oxidation of the substances. This procedure is suitable, however, for analyzing chemically stable compounds such as hydrocarbons or chlorinated solvents.

Finally, it can be carried out with high-purity gas from a gas reservoir. The gas reservoir is generally a vessel which is closed by a septum and which is connected by a gas line to a gas vial. In this procedure, the substances are again transferred gently into the appliance, but an additional gas reservoir is required.

In all three procedures, care must be taken to ensure that, when inserting the needle into the pressurized injector of the chromatograph, gas flows back through the filter into the syringe or into the gas delivery system, since otherwise there is a danger of the substances being desorbed in the wrong direction.

This would lead to incorrect results and to so-called carry-over effects, i.e. carry-over of substances from one measurement to the next. This effect can generally be avoided by the pressure in the gas chromatograph being cut off during the injection. This is also advisable since in this way the substances can be transported in the smallest possible amount of gas from the filter into the chromatograph, and the gas in which the substances are transported into the chromatograph is not diluted by the regular gas flow in the chromatograph. The smaller the amount of desorption gas, the sharper the signals and, accordingly, the higher the sensitivity of the equipment.

The invention claimed is:

1. A method for preparation of a gaseous sample while being drawn through a hollow needle into a syringe for extraction and enrichment of a volatile component from the gaseous sample for subsequent introduction into an analytical device, whereby for extraction of an analyte of interest the sample is flushed through a packing of an extraction material between two hoops contained in an extraction tube, the extraction tube comprising a heating jacket, being located between the hollow needle and the syringe, and having an increased volume compared to the interior of the needle, wherein extraction and enrichment of the volatile component from the sample comprises:
injecting the needle connected to the syringe into a gas space within a sample vial containing a liquid sample;
intaking a portion of the gas space into the syringe through the packing of extraction material located between the needle and the syringe so that a portion of the analyte of interest of the sample is adsorbed onto the extraction material;
immersing a tip of the needle into the liquid sample after intaking;
expelling gas from within the syringe through the extraction material and through the needle back into the sample when the tip of the needle is immersed within the sample;
drawing back the tip of the needle away from the sample back into the gas space after expelling; and
repeating the steps of intaking, immersing, expelling and drawing to increase an extraction efficiency of the analyte from the gas space within the sample vial containing the sample into the extraction material.

2. The method of claim 1, wherein the analytical device comprises a gas chromatograph.

* * * * *

UNITED STATES PATENT AND TRADEMARK OFFICE
CERTIFICATE OF CORRECTION

PATENT NO. : 9,146,216 B2  
APPLICATION NO. : 10/581951  
DATED : September 29, 2015  
INVENTOR(S) : Beat Schilling et al.

Page 1 of 1

It is certified that error appears in the above-identified patent and that said Letters Patent is hereby corrected as shown below:

On the Title Page:
Item (22); change "Dec. 15, 2004" to --Nov. 15, 2004--

Signed and Sealed this
Twelfth Day of April, 2016

Michelle K. Lee
*Director of the United States Patent and Trademark Office*